(12) United States Patent
Kim et al.

(10) Patent No.: US 8,153,154 B2
(45) Date of Patent: Apr. 10, 2012

(54) ARGININE-CONJUGATED BIOREDUCIBLE POLY(DISULFIDE AMINE) POLYMERS FOR GENE DELIVERY SYSTEMS

(75) Inventors: Sung Wan Kim, Salt Lake City, UT (US); Tae-il Kim, Salt Lake City, UT (US)

(73) Assignee: University of Utah, Salt Lake City, UT (US)

( * ) Notice: Subject to any disclaimer, the term of this patent is extended or adjusted under 35 U.S.C. 154(b) by 404 days.

(21) Appl. No.: 12/370,515

(22) Filed: Feb. 12, 2009

(65) Prior Publication Data

US 2009/0233365 A1    Sep. 17, 2009

Related U.S. Application Data

(60) Provisional application No. 61/028,131, filed on Feb. 12, 2008.

(51) Int. Cl.
*A61K 9/14* (2006.01)
*C07H 21/04* (2006.01)

(52) U.S. Cl. ........................ 424/486; 536/23.1; 536/24.5

(58) Field of Classification Search ........................ None
See application file for complete search history.

(56) References Cited

U.S. PATENT DOCUMENTS

2004/0209832 A1* 10/2004 McSwiggen et al. ........... 514/44
2010/0010067 A1*  1/2010 Kim et al. ................... 514/44 A

OTHER PUBLICATIONS

Choi et al., Journal of Controlled Release 99 (2004) 445-456.*
Lin et al., Bioconjugate Chemistry 18 (2007) 138-145.*
Tae-Il Kim, Mei Ou, Minhyung Lee, Sung Wan Kim, Arginine-grafted bioreducible poly(disulfide amine) for gene delivery systems, Biomaterials 30 (2009) 568-664.
Sung Wan Kim, Ji Hoon Jeong, Tae-Il Kim, Sung Wan Kim, David A. Bull, VEGF siRNA Delivery System Using Arginine-Grafted Bioreducible Poly(disulfide amine), American Chemical Society, Molecular Pharmaceutics, Dec. 4, 2008, http://pubs.acs.org.

* cited by examiner

*Primary Examiner* — Doug Schultz
(74) *Attorney, Agent, or Firm* — Clayton, Howarth & Cannon, P.C.

(57) ABSTRACT

An arginine-grafted bioreducible poly(disulfide amine) ("ABP") as a reagent for efficient and nontoxic gene delivery is described. ABP forms positively charged nano-particles of less than 200 nm with plasmid DNA. ABP is biodegraded under reducing conditions, such as the cytoplasm. ABP exhibits much higher transfection efficiency than polyethyleneimine in mammalian cells and exhibits no cytotoxicity.

10 Claims, 6 Drawing Sheets

ARGININE-CONJUGATED BIOREDUCIBLE POLY(DISULFIDE AMINE) POLYMERS FOR GENE DELIVERY SYSTEMS

CROSS-REFERENCE TO RELATED APPLICATIONS

This application claims the benefit of U.S. Provisional Application No. 61/028,131, filed Feb. 12, 2008, which is hereby incorporated by reference in its entirety.

STATEMENT REGARDING FEDERALLY SPONSORED RESEARCH OR DEVELOPMENT

This invention was made with government support under grant no. DK 077703 from the National Institutes of Health. The government has certain rights in the invention.

BACKGROUND OF THE INVENTION

This invention relates to non-viral gene delivery carriers. More particularly, this invention relates to arginine-conjugated bioreducible poly(disulfide amine) polymers as gene delivery carriers.

Development of non-toxic and efficient gene delivery carriers is one of the most important requirements for gene therapy. So far, numbers of non-viral gene delivery carriers based on lipids and polymers have been developed as alternatives of viral gene delivery carriers. They have advantages such as non-immunogenicity, convenience of handling, and unlimited delivery capacity of genetic materials over viral vectors. J. S. Remy et al., Gene transfer with lipospermines and polyethyleneimines, 30 Adv. Drug Deliv. Rev. 85-95 (1998); F. Liu & L. Huang, Development of non-viral vectors for systemic gene delivery, 78 J. Control. Release 259-266 (2002); D. Luo & W. M. Saltzman, DNA delivery systems, 18 Nat. Biotechnol. 33-37 (2000). Among them, polymeric gene delivery carriers have multi-functional groups modifiable with biofunctional moieties in their backbones. T. G. Park, J. H. Jeong & S. W. Kim, Current status of polymeric gene delivery systems, 58 Adv. Drug Deliv. Rev. 467-486 (2006). Despite the advantages, their applications to human gene therapy have been limited because of their cytotoxicity and unsatisfactory transfection efficiency. S. Y. Wong et al., Polymer systems for gene delivery-past, present, and future, 32 Prog. Polym. Sci. 799-837 (2007).

Thus, while prior non-viral gene delivery systems are known and are generally suitable for their limited purposes, they possess certain inherent deficiencies that detract from their overall utility.

In view of the foregoing, it will be appreciated that providing arginine-conjugated bioreducible poly(disulfide amine) polymers as gene delivery carriers would be a significant advancement in the art.

BRIEF SUMMARY OF THE INVENTION

An illustrative gene delivery carrier according to the present invention comprises an arginine-grafted bioreducible polymer. In another illustrative embodiment, the arginine-grafted bioreducible polymer comprises a poly(disulfide amine) polymer.

In still another illustrative embodiment, the gene delivery carrier is represented by the formula wherein n is about 1 to about 1000; $R^1$ is $(CH_2)_m NH$, wherein m is about 1 to about 18; and $R^2$ is an arginine residue. Illustrative examples of $R^1$ include $(CH_2)_6 NH$, $(CH_2)_4 NH$, and $(CH_2)_2 NH$.

Still another illustrative embodiment of the invention comprises a complex comprising a selected nucleic acid bonded to an arginine-grafted bioreducible polymer. For example, the arginine-grafted bioreducible polymer can comprise a poly(disulfide amine) polymer. By way of further example, the arginine-grafted bioreducible polymer can be represented by the formula wherein n is about 1 to about 1000; $R^1$ is $(CH_2)_m NH$, wherein m is about 1 to about 18; and $R^2$ is an arginine residue. Illustrative examples of $R^1$ include $(CH_2)_6 NH$, $(CH_2)_4 NH$, and $(CH_2)_2 NH$. Illustratively, the selected nucleic acid can comprise a plasmid, siRNA, or an oligonucleotide.

In yet another illustrative embodiment of the invention, a method for transfecting mammalian cells comprises contacting selected mammalian cells with a complex comprising a selected nucleic acid bonded to an arginine-grafted bioreducible polymer. For example, the arginine-grafted bioreducible polymer can comprise a poly(disulfide amine) polymer. By way of another example, the arginine-grafted bioreducible polymer can be represented by the formula wherein n is about 1 to about 1000; $R^1$ is $(CH_2)_m NH$, wherein m is about 1 to about 18; and $R^2$ is an arginine residue. Illustratively, $R^1$ can comprise $(CH_2)_6 NH$, $(CH_2)_4 NH$, or $(CH_2)_2 NH$, and the selected nucleic acid can comprise a plasmid, siRNA, or an oligonucleotide.

An illustrative method of making an arginine-conjugated bioreducible polymer according to the present invention comprises grafting protected arginine residues to a bioreducible polymer and then removing the protecting groups from the grafted arginine residues.

BRIEF DESCRIPTION OF THE SEVERAL VIEWS OF THE DRAWINGS

FIGS. 2A-C show results of agarose gel electrophoresis of plasmid DNA ("pDNA") mixed with ABP in the absence (FIG. 2A) and presence (FIG. 2B) of 2.5 mM dithiothreitol ("DTT").

DETAILED DESCRIPTION

Before the present arginine-conjugated bioreducible poly (disulfide amine) polymer and methods are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise.

Unless defined otherwise, all technical and scientific terms used herein have the same meanings as commonly understood by one of ordinary skill in the art to which this invention belongs.

In describing and claiming the present invention, the following terminology will be used in accordance with the definitions set out below.

As used herein, "comprising," "including," "containing," "characterized by," and grammatical equivalents thereof are inclusive or open-ended terms that do not exclude additional, unrecited elements or method steps. "Comprising" is to be interpreted as including the more restrictive terms "consisting of" and "consisting essentially of." As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

An arginine-grafted bioreducible poly(CBA-DAH) ("ABP") polymer was synthesized for use as a reagent for non-viral gene delivery. ABP formed positively charged nano-particles (less than 200 nm) with pDNA, which are biodegradable in a reducing environment, such as the cytoplasm. The biodegradation of ABP by reductive cleavage can facilitate the efficient release of pDNA from polyplexes and reduce its cytotoxicity, which was found to be very low. ABP showed much higher transfection efficiency than polyethylenimine ("PEI25k") and the backbone polymer (i.e., CBA-DAH) in mammalian cells. In the presence of serum, transfection efficiency of ABP was not reduced much, unlike PEI25k, suggesting that ABP can be also used as an efficient gene delivery carrier for in vivo systems. The transfection efficiency of ABP was not improved by chloroquine treatment, and the cellular uptake pattern of ABP/pDNA polyplexes showed no significant difference from that of poly (CBA-DAH). These results suggest that ABP can act as an endosome buffer and that the greatly enhanced transfection efficiency of ABP is not due to its high cellular penetrating ability but may be mediated by other factors, such as good nuclear localization ability. Therefore, arginine-conjugation to a linear polymer appeared to be very effective, and ABP is an efficient and nontoxic carrier for gene delivery systems.

EXAMPLES

Materials

Hyperbranched poly(ethylenimine) (bPEI, 25 kDa), tert-Butyl-N-(6-aminohexyl)carbamate (N-Boc-1,6-diaminohexane, N-Boc-DAH), trifluoroacetic acid (TFA), triisopropylsilane, triisobutylsilane, dithiothreitol (DTT), N,N-diisopropylethylamine (DIPEA), piperidine, 3-[4,5-dimethylthiazol-2-yl]-2,5-diphenyltetrazolium bromide (MTT), chloroquine diphosphate salt, and trypan blue solution (0.4%) were purchased from Sigma-Aldrich (St. Louis, Mo.). N,N'-cystaminebisacrylamide (CBA) was purchased from PolySciences, Inc. (Warrington, Pa.). 2-(1H-benzotriazole-1-yl) 1,1,3,3-tetramethyluronium hexafluorophosphate (HBTU) was purchased from Novabiochem (San Diego, Calif.). Fmoc-L-Arg(pbf)-OH was purchased from Anaspec, Inc. (San Jose, Calif.). The plasmid pCMV-Luc, containing a firefly luciferase reporter gene was amplified in $E.\ coli$ DH5α and isolated with a Maxiprep kit (Invitrogen, Carlsbad, Calif.). Luciferase assay system and reporter lysis buffer were purchased from Promega (Madison, Wis.). Fetal bovine serum (FBS), Dulbecco's phosphate buffered saline (DPBS), and Dulbecco's modified Eagle's medium (DMEM) were purchased from Invitrogen. BCA™ protein assay kit was purchased from Pierce (Rockford, Ill.). YOYO-1 iodide (1 mM solution in DMSO) was purchased from Molecular Probes (Eugene, Oreg.). All other chemicals were purchased and used without any further purification.

Example 1

Synthesis and Characterization of ABP

Arginine-grafted bioreducible poly(disulfide amine) (ABP) was synthesized using poly(CBA-DAH) as a backbone polymer. Poly-(CBA-DAH) was selected as a bioreducible backbone polymer because it has modifiable amine groups and showed high transfection efficiency in various cell lines. M. Ou, X. L. Wang, R. Xu, C. W. Chang, D. A. Bull & S. W. Kim, Novel biodegradable poly(disulfide amine)s for gene delivery with high efficiency and low cytotoxicity, 19 Bioconjug. Chem. 626-633 (2008). Briefly, poly(CBA-DAH) was synthesized using N-Boc-DAH and CBA as repeated monomers. Then, 4 equivalents of Fmoc-Arg(pbf)-OH and HBTU, and 8 equivalents of DIPEA were used for arginine-graft reaction of poly(CBA-DAH) in DMF. Then, protecting groups of arginines were removed.

In more detail, the backbone poly(disulfide amine) polymer, poly(CBA-DAH) was synthesized by Michael reaction of equivalent moles of N-Boc-DAH and CBA in MeOH/H$_2$O solution (9:1, v/v), according to the method described in U.S. patent application Ser. No. 12/267,015. The polymerization reaction was maintained in the dark under a nitrogen atmosphere at 60° C. for 5 days. Then, 10% mole of N-Boc-DAH was added to the reaction mixture to consume unreacted acrylamide functional groups, and the reaction was further conducted for 2 days. After precipitation with diethyl ether, the Boc groups of the product were removed by the reagent solution (TFA:triisobutylsilane:H$_2$O=95:2.5:2.5, v/v) at ice bath temperature for 30 min. After additional precipitation with diethyl ether, the polymer product was dialyzed against ultra-pure water with dialysis membrane (MWCO=1000, Spectrum Laboratories, Inc., Rancho Dominguez, Calif.), followed by lyophilization to leave poly(CBA-DAH) as a sticky solid.

Figure 1:
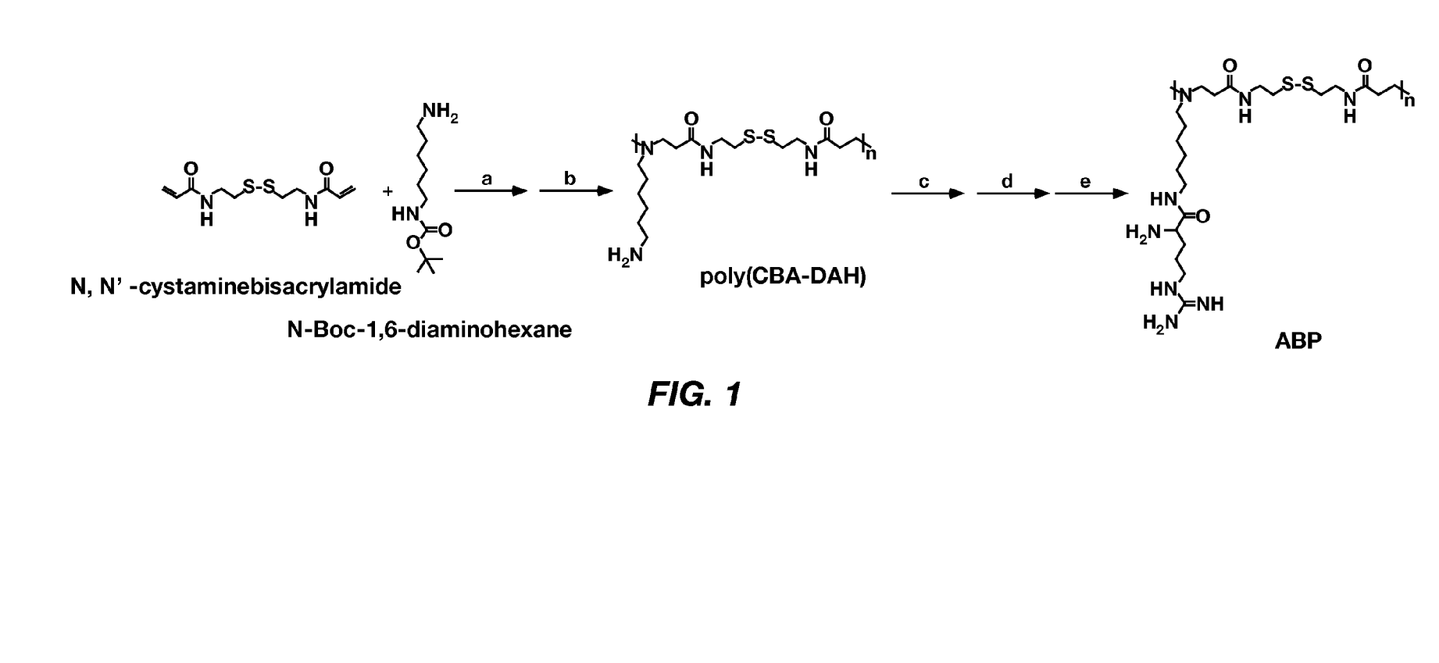
FIG. 1 shows a scheme for synthesis of an illustrative embodiment of an arginine-conjugated bioreducible poly (disulfide amine) polymer ("ABP") according to the present invention.

Then, grafting of arginine onto poly(CBA-DAH) was performed using 4 equivalents of Fmoc-Arg(pbf)-OH and HBTU, and 8 equivalents of DIPEA in DMF at room temperature for 2 days. Then, the reaction product was precipitated with an excess of diethyl ether twice to remove unreacted reagents, and mixed with an equal volume of piperidine solution (30% in DMF) at room temperature for 30 min to remove the Fmoc groups of grafted Fmoc-Arg(pbt)-OH. After two additional precipitations with ether, the reagent solution (TFA:triisopropylsilane:H$_2$O=95:2.5:2.5, v/v) was added to the precipitates in order to deprotect the pbf groups of arginine residues at room temperature for 30 min. After another precipitation with ether, the final product, arginine-grafted bioreducible poly(disulfide amine) (ABP) was dialyzed against ultra-pure water overnight and lyophilized before use for analysis and assay. FIG. 1 shows the synthetic scheme of ABP.

The synthesis of ABP was confirmed by $^1$H NMR (400 MHZ, D20), as follows.

ABP; $^1$H NMR (D$_2$O): δ (NCH$_2$CH$_2$CH$_2$CH$_2$CH$_2$NHCO)=1.24, δ (NCH$_2$CH$_2$CH$_2$CH$_2$CH$_2$NHCO, arginine(NH$_2$CHCH$_2$CH$_2$CH$_2$NH))=1.41-1.53, δ arginine(NH$_2$CHCH$_2$CH$_2$CH$_2$NH)=1.72, δ (NCH$_2$CH$_2$CONH)=2.59, δ (CH$_2$SSCH$_2$)=2.74, δ (NCH$_2$CH$_2$CH$_2$CH$_2$CH$_2$NHCO)=2.88, δ (NCH$_2$CH$_2$CONH, NCH$_2$CH$_2$CH$_2$CH$_2$CH$_2$CH$_2$NHCO, arginine(NH$_2$CHCH$_2$CH$_2$CH$_2$NH))=3.10-3.18, δ (NCH$_2$CH$_2$CONHCH$_2$)=3.41, δ arginine(NH$_2$CHCH$_2$CH$_2$CH$_2$NH)=3.71.

It was found from the calculation of ratio between the integration of arginine proton peaks and the integration of poly(CBA-DAH) proton peaks that almost 100% of the primary amines of poly(CBADAH) were modified with arginine residues.

The molecular weight of ABP was estimated by size-exclusion chromatography (SEC) (Superdex 75 column, calibrated with standard poly[N-(2-hydroxypropyl)-methacrylamide] (pHPMA)) using AKTA FPLC system. ABP was dissolved at a concentration of 3 mg/mL. ABP was eluted with 0.1 M acetate buffer (30% Acetonitrile, v/v, pH 5.5). Flow rate was 0.4 mL/min. The Mw of ABP was estimated to be 4.45×10$^3$ Da/mole and its PDI value was 1.49. The Mw of the backbone polymer, poly(CBA-DAH), was reported to be 3.52 kDa/mole in M. Ou et al., supra. With the assumption that 100% primary amines of ABP were modified with arginines, the experimental Mw value of ABP was revealed to be lower than the theoretical value. In general, positively charged cationic polymers are known to have a tendency to appear smaller than they really are in SEC because they may interact with the column and, consequently, they are eluted slowly. Therefore, this result may be due to the strong positive charges of ABP. A higher PDI value of ABP than that of poly(CBA-DAH) (1.13) is also thought to be induced by this interaction.

Example 2

Agarose Gel Electrophoresis

Agarose gel electrophoresis was performed to examine pDNA condensing ability of ABP in the absence or presence of DTT. ABP has internal disulfide bonds and it is expected to be degraded in reducing environments such as cytoplasm, which contains 0.110 mm glutathione. DTT is a well-known reducing agent. ABP polyplexes were incubated in 2.5 mM DTT for 1 h to investigate the susceptibility to bioreducing intracellular environments of ABP polyplexes.

Agarose gel electrophoresis was used to examine pDNA condensing ability of ABP. ABP polyplexes were prepared in Hepes-buffered saline (10 mm Hepes, 1 mm NaCI, pH 7.4) at various weight ratios ranging from 0.5 to 20. Agarose gel (0.7%, w/v) containing ethidium bromide solution (0.5 μg/mL) was prepared in TAE (Tris-Acetate-EDTA) buffer. After 30 min of incubation at room temperature, the samples were electrophoresed at 100 V for 30 min. Identically prepared ABP polyplexes were incubated in the presence of 2.5 mm DTT for 1 h at room temperature and then electrophoresed. In this case, poly(CBA-DAH) polyplexes were used as controls. The location of pDNA bands was visualized with a UV illuminator (Gel Documentation Systems, Bio-Rad, Hercules, Calif.).

Figure 2A:
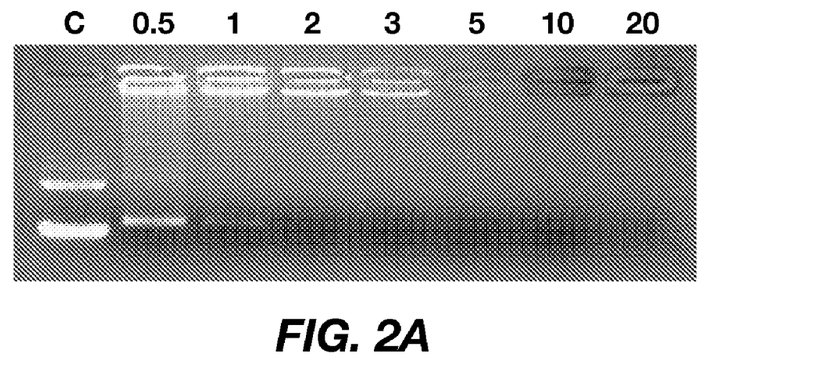

As shown in FIG. 2A, ABP can retard pDNA completely from a weight ratio of 2 in the absence of DTT. This result shows that ABP can condense pDNA well via electrostatic interaction between positive charges of ABP and negative charges of pDNA phosphates.

Figure 2B:
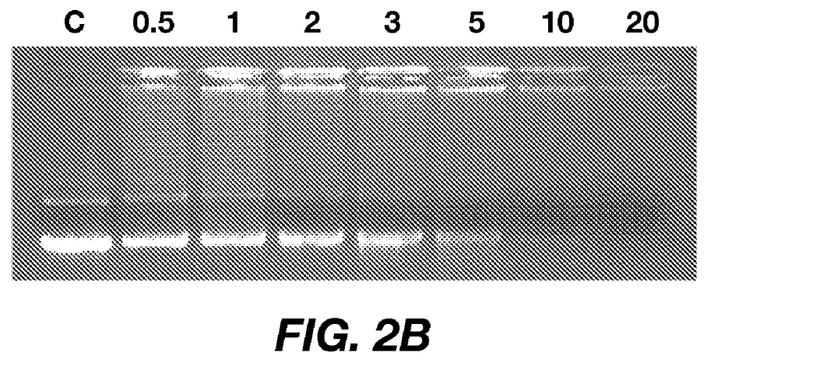

On the other hand, pDNA released from ABP polyplex was observed even at a weight ratio of 10 in the presence of 2.5 mm DTT (FIG. 2B). This means that ABP is degraded in reducing environments and thereafter it cannot condense pDNA because of bioreducible cleavage of internal disulfide bonds. Consequently, it is expected that ABP polyplexes can release pDNA by bio-reduction in cytoplasm, which may lead to efficient transfection.

Figure 2C:
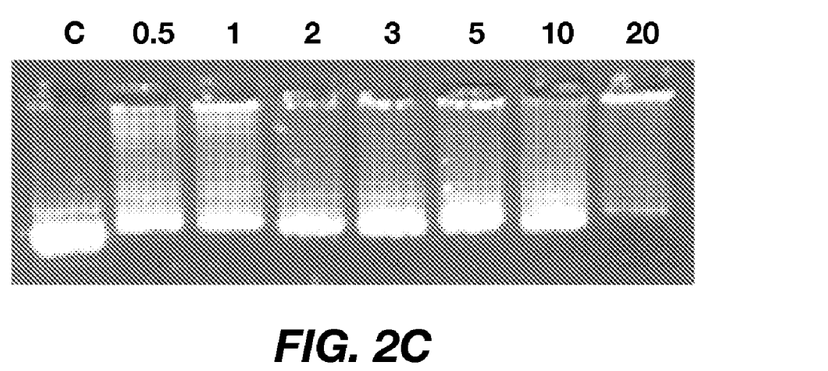
FIG. 2C shows results obtained with pDNA/poly (CBA-DAH) polyplexes in the presence of 2.5 mM DTT. Lanes C are controls containing only pDNA, and the reference numerals for other lanes indicate weight ratios of ABP (FIGS. 2A-B) or poly(CBA-DAH) (FIG. 2C) to pDNA.

ABP was still able to retard pDNA at a weight ratio of 20 even in the presence of DTT. In contrast with ABP, it was observed that poly(CBA-DAH) could not condense pDNA at the same weight ratio in the presence of DTT (FIG. 2C). Higher molar ratios of poly(CBA-DAH) were used in each poly(CBA-DAH)-containing polyplex than those of ABP-containing polyplexes at the same weight ratio, because the molecular weight of poly(CBA-DAH) is less than that of ABP. From this result, it is thought that ABP can form more stable polyplexes than poly(CBA-DAH). Considering the structural differences between ABP and poly(CBA-DAH), it may be that grafted arginine residues help ABP form stable polyplexes with pDNA due to their strong positive charges. In general, linear biodegradable polymers are degraded into two molecules via just one cleavage of a backbone bond. Their fast degradation rate is believed to result in low levels of gene delivery to the cell nucleus. Therefore, cross-linked biodegradable polymers have been developed to overcome this handicap of linear polymers for efficient gene delivery because one cleavage of a backbone bond does not lead to the break of whole polymer structure in cross-linked polymers. Y.-b. Lim et al., Biodegradable endosome disruptive, and cationic network-type polymer as a highly efficient and non-toxic gene delivery carrier, 13 Bioconjug. Chem. 952-957 (2002); T.-i. Kim et al., Synthesis of biodegradable cross-linked poly(β-amino ester) for gene delivery and its modification, inducing enhanced transfection efficiency and stepwise degradation, 16 Bioconjug. Chem. 1140-1148 (2005). Thus, this lower susceptibility to bio-reduction of ABP may contribute to its higher transfection efficiency than poly(CBA-DAH), although ABP is a linear polymer.

Example 3

Average Sizes and Zeta-Potential Measurements

The average sizes and Zeta-potentials of ABP polyplexes were measured because polyplexes are thought to need an appropriate size for efficient uptake into cells, and a net positive charge of a polyplex is thought to be helpful for its absorption to negatively charged cellular membrane, also leading to efficient intracellular trafficking. D. W. Pack et al., Design and development of polymers for gene delivery, 4 Nat. Rev. Drug Discov. 581-593 (2005). Backbone polymer, poly(CBA-DAH), was used as a control.

The average sizes of ABP and poly(CBA-DAH) polyplexes were examined using a Zetasizer 3000 (Malvern Instruments, USA) with a He—Ne Laser beam (633 nm, fixed scattering angle of 90°) at 25° C. Polyplex solutions (10 μg of pDNA in 0.5 mL) were prepared in Hepes buffered saline (10 mm Hepes, 1 mm NaCI, pH 7.4) at various weight ratios ranging from 0.5 to 20. After 30 min of incubation, polyplex solutions were diluted to a final volume of 4 mL before measurement. Measured sizes were presented as the average values of 5 runs.

Figure 3:
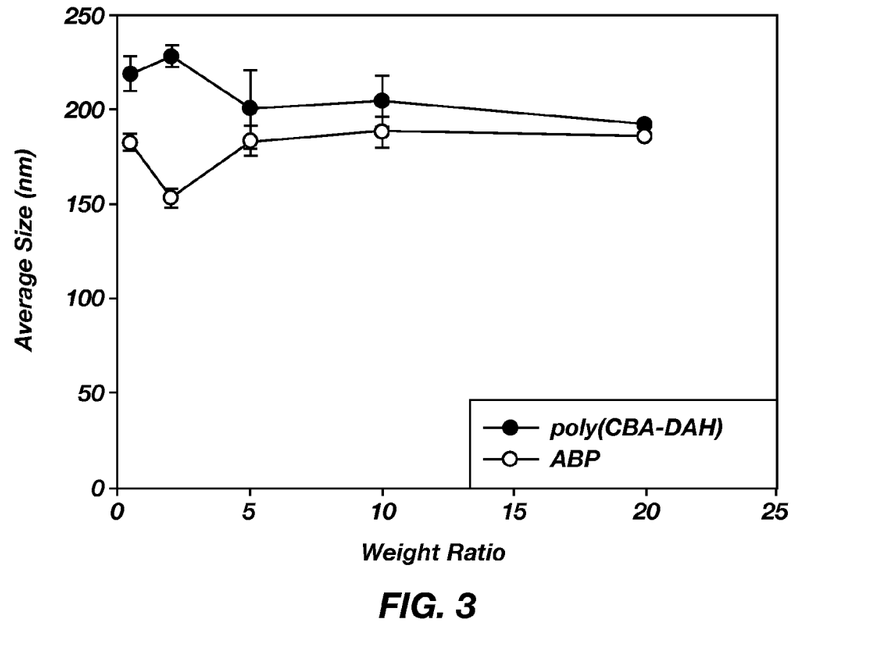
FIGS. 3 and 4 show the average sizes (FIG. 3) and zeta-potential values (FIG. 4) of pDNA/ABP (○) and pDNA/poly (CBA-DAH) (●) polyplexes.

ABP polyplexes displayed average sizes less than 200 nm at all weight ratios used (FIG. 3). Below a weight ratio of 5, some differences were found in average sizes of both polymers but no significant differences over a weight ratio of 5 were observed. This result shows that ABP can condense pDNA into nano-sized particles appropriate for gene delivery.

Figure 4:
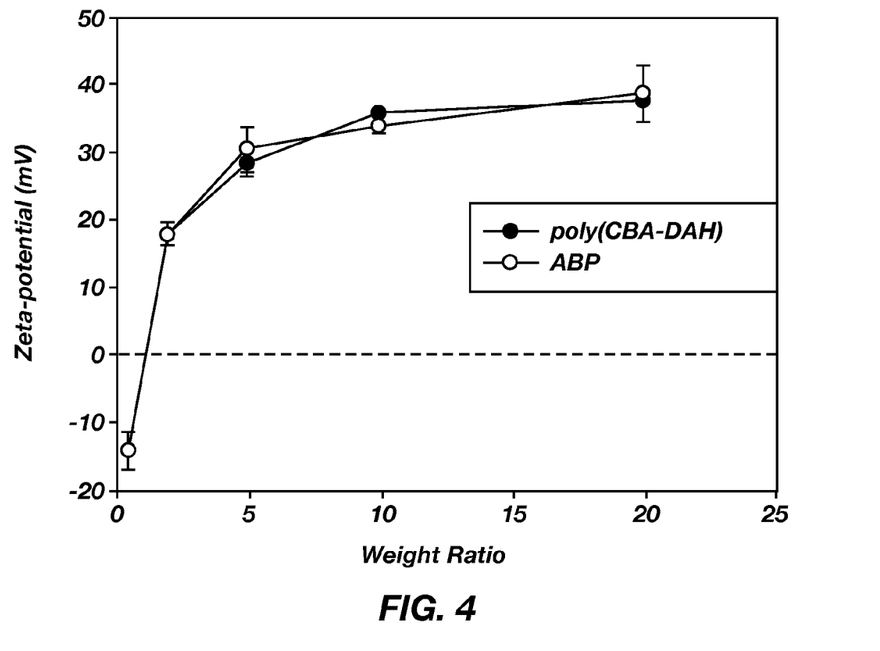

Zeta-potential measurements of polyplexes were also carried out using a Zetasizer 3000 at 25° C. ABP and poly(CBA-DAH) polyplexes were prepared by the same method as in the size measurement experiments. Potential values were presented as the average values of 3 runs. As shown in FIG. 4, ABP polyplex displayed a negative value (−15 mV) at a weight ratio of 1, suggesting that a stable polyplex is not formed at that ratio, which is consistent with the agarose gel electrophoresis results (Example 2). Zeta-potential values of ABP polyplexes increased gradually according to the increase of polyplex weight ratios, finally reaching positive plateau values (30-40 mV) from a weight ratio of 10. Zeta-potential values of ABP and poly(CBA-DAH) polyplexes showed no significant differences between them. These results suggest that ABP forms positively charged polyplexes that can mediated efficient transfection and that the polyarginine grafted onto poly(CBA-DAH) does not affect the size or Zeta-potential values of polyplexes.

Example 4

Cytotoxicity

MTT assay was performed to examine the cytotoxicity of polyplexes. C2C12 mouse myoblast cells were seeded in a 96-well tissue culture plate at $1\times10^4$ cells/well in 90 µL DMEM medium containing 10% FBS. Cells achieving 70-80% confluence after 24 h were exposed to 10 µL of the polyplex solutions (0.5 µg pDNA) at different weight ratios for 4 h in serum-free DMEM medium. After exchange of medium for fresh DMEM medium containing 10% FBS, the cells were further maintained for 48 h. Then, 25 µL of stock solution of MTT (2 mg/ml in PBS) was added to each well. After 2 h of incubation at 37° C., the medium was removed carefully and 150 µL of DMSO was added to each well to dissolve the formazan crystal formed by proliferating cells. Absorbance was measured at 570 nm using a microplate reader (Model 680, Bio-Rad Lab, Hercules, Calif.) and recorded as a percentage relative to untreated control cells. All experiments were performed in quadruplicate.

Figure 5:
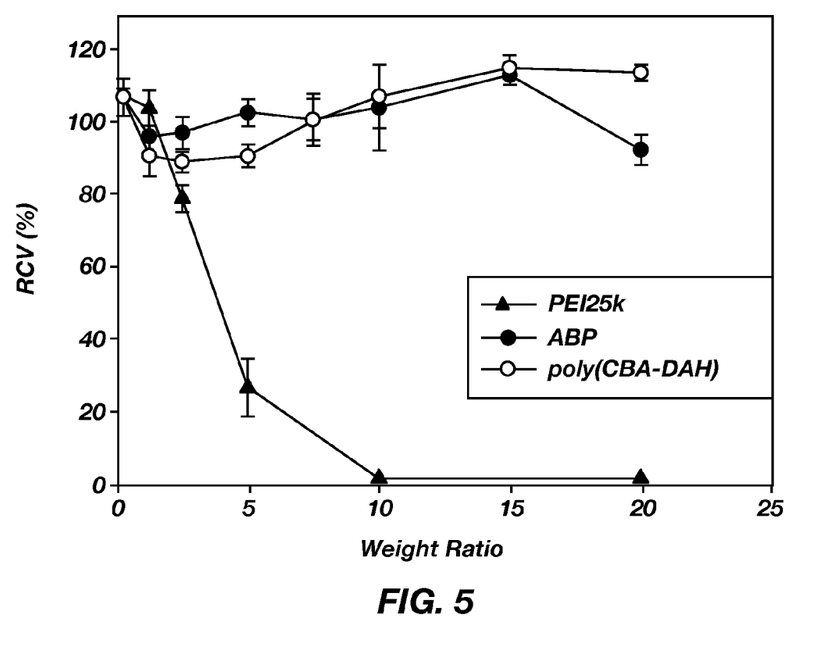
FIG. 5 shows results of cytotoxicity assays of polyplexes in C2C12 cells; data are expressed as relative cell viability ("RCV") as a function of weight ratio of carrier (▲—PEI25k, ●—ABP, ○—poly(CBA-DAH) to pDNA.

As shown in FIG. 5, ABP polyplexes were observed to exhibit no significant cytotoxicity (RCV >90%) compared to poly(CBA-DAH), even at a weight ratio of 80 in C2C12 cells. The reason for this low cytotoxicity may be that ABP can be degraded into non-toxic small molecules in cells. The cytotoxicity of PEI25k was found to be very high, as is well-known.

These results suggest that ABP can be used for gene delivery.

Example 5

In Vitro Transfection

In vitro transfection experiments were performed using a luciferase reporter gene in C2C12 mouse myoblast cells and NIH3T3 mouse embryonic fibroblasts cells. PEI25k and poly(CBA-DAH) were used as controls. Polyplexes of PEI25k and poly(CBA-DAH) were prepared at weight ratios of 1 and 40, respectively.

More particularly, C2C12 and NIH3T3 cells were seeded at a density of $5\times10^4$ cells/well in a 24-well plate in DMEM medium containing 10% FBS and grown to reach 70-80% confluence prior to transfection. Before transfection, the medium in each well was exchanged for fresh serum-free medium. For transfection in serum, the medium was not exchanged at this time. The cells were treated with polyplex solutions (0.5 µg pDNA) at different weight ratios for 4 h at 37° C. After exchange with fresh medium containing 10% FBS, cells were further incubated for 2 days before assay. Then, the growth medium was removed and the cells were rinsed with DPBS and shaken for 30 min at room temperature in 120 µL of Reporter Lysis Buffer. Luciferase activity was measured by a luminescence assay, and a protein quantification assay was performed using a BCA™ Protein Assay Reagent Kit. The luciferase activity of 25 µL of cell lysate was measured with 100 µL of luciferase assay reagent on a luminometer (Dynex Technologies Inc., Chantilly, Va.). The final results were reported in terms of RLU/mg cellular protein. All experiments were performed in triplicate.

Figure 6:
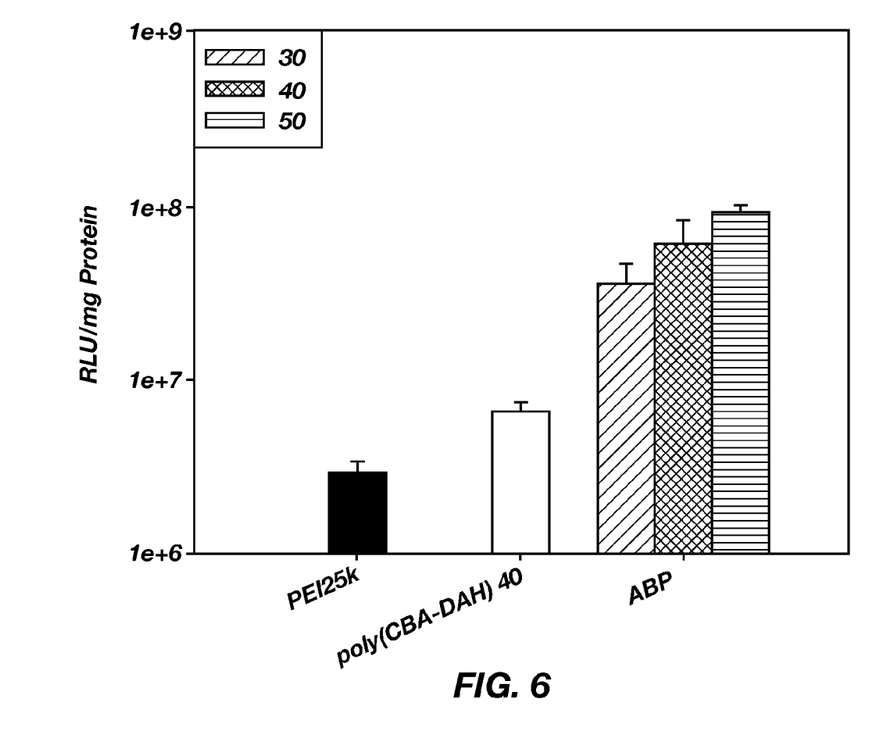
FIGS. 6 and 7 shows the relative transfection efficiencies of a polyethylenimine control (dark bars, "PEI25k"), poly (CBA-DAH) (open bars), and ABP (hatched bars) as a function of the weight ratio of carrier to pDNA in C2C12 cells (FIG. 6) and NIH3T3 cells (FIG. 7); numbers in the boxes indicate the weight ratios of the pDNA/ABP polyplexes.
Figure 7:
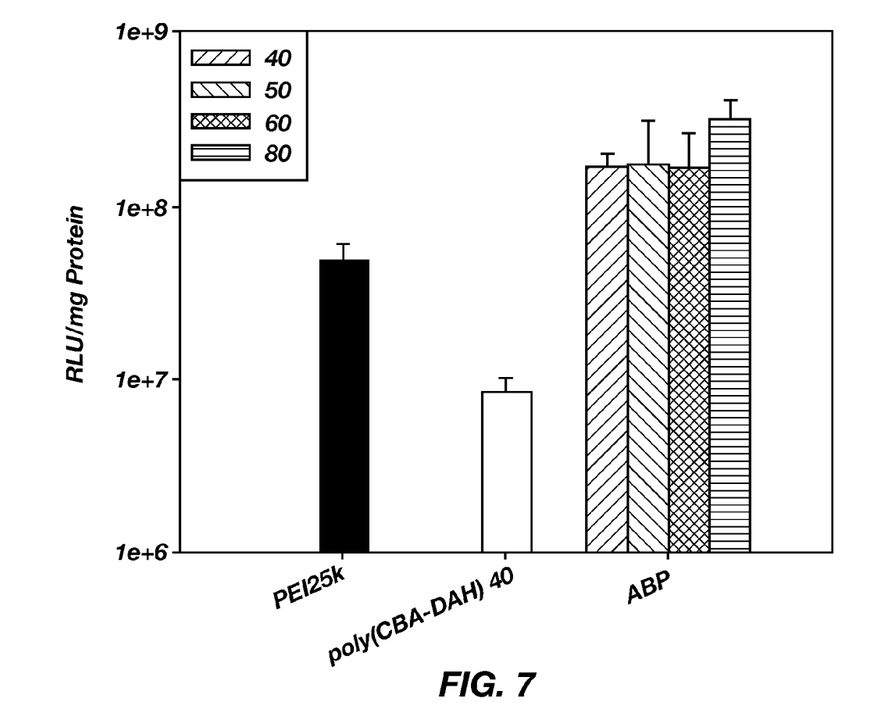

FIG. 6 shows the result in C2C12 cells in the absence of serum. The transfection efficiency of ABP at a weight ratio of 50 was found to be about 30 times higher than that of PEI25k. ABP displayed about 9 times and 14 times higher transfection efficiency than poly(CBA-DAH) at weight ratios of 40 and 50, respectively. In FIG. 7, ABP showed about 3-6 times higher transfection efficiency than PEI25k and 20-37 times higher transfection efficiency than poly(CBA-DAH) in NIH3T3 cells in the absence of serum.

Figure 8:
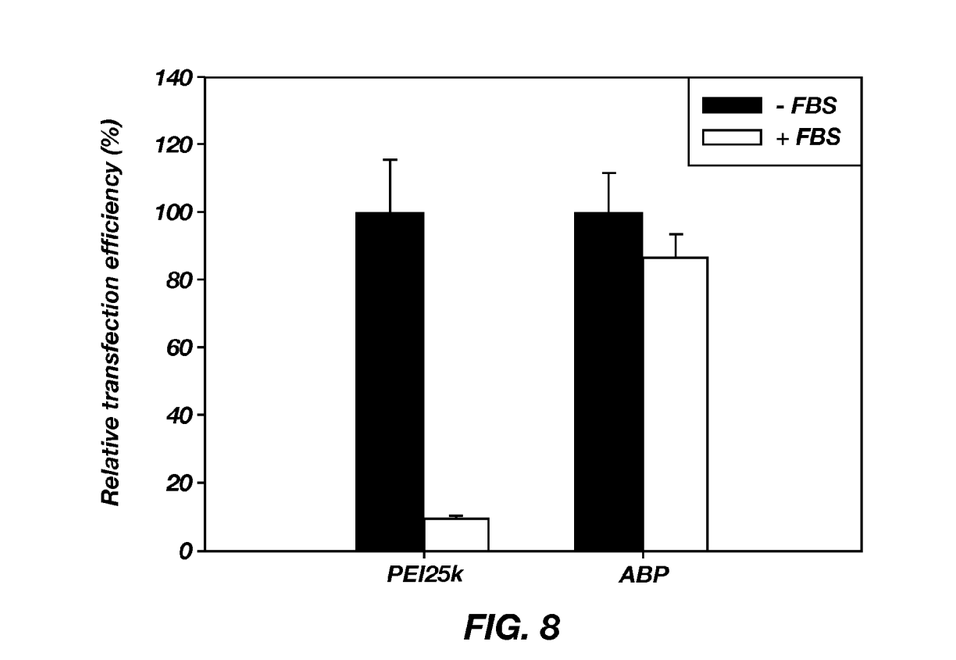
FIG. 8 shows relative transfection efficiency in C2C12 cells of pDNA/PEI25k ("PEI25k") and pDNA/ABP ("ABP") polyplexes in the absence (dark bars) and presence (open bars) of fetal bovine serum ("FBS"). Relative transfection efficiency is the ratio, expressed as a percentage, of transfection efficiency with serum to transfection efficiency without serum.

In the presence of serum, the transfection efficiency of ABP was reduced just 15% in comparison with its efficiency in the absence of serum, although PEI25k showed a 90% reduction in efficiency in C2C12 cells (FIG. 8). This result means that the transfection process of ABP will not be seriously inhibited from serum interaction and that ABP has potential as a gene delivery systems in vivo as well as in vitro.

These results also show that arginine grafted to linear poly (CBA-DAH) can greatly increase the transfection efficiency of the polymer.

Example 6

Transfection Mechanisms Study

A series of transfection experiments were performed to examine the transfection mechanism of ABP polyplexes. First, 100 µM chloroquine was added to the cells before treatment of polyplexes and the cells were further incubated for 4 h during transfection. Chloroquine is a well-known endosome disrupting agent which can facilitate the release of polyplexes from endosome and lead to enhanced transfection. K. Ciftci & R. J. Levy, Enhanced plasmid DNA transfection with lysosomotropic agents in cultured fibroblasts, 218 Int. J. Pharm. 81-92 (2001). PEI25k was used as a control.

More particularly, transfection experiments were performed with or without chloroquine order to examine the cellular uptake mechanism of ABP polyplex. C2C12 cells were seeded at a density of $5\times10^4$ cells/well in a 24-well plate in DMEM medium containing 10% FBS and grown to reach 70-80% confluence prior to transfection. Each polyplex was prepared with 0.5 µg of pDNA at a fixed weight ratio (PEI: 1, ABP: 40). Then, the cells were treated with 100 µM chloroquine before transfection, and the cells were incubated in the presence or absence of chloroquine during transfection. After 4 h of incubation, all the cells were washed with DPBS and maintained in DMEM containing 10% FBS at 37° C. for 2 days. Further experiments and assays were performed by the same transfection method mentioned above in the absence of serum. All experiments were performed in triplicate.

Figure 9:
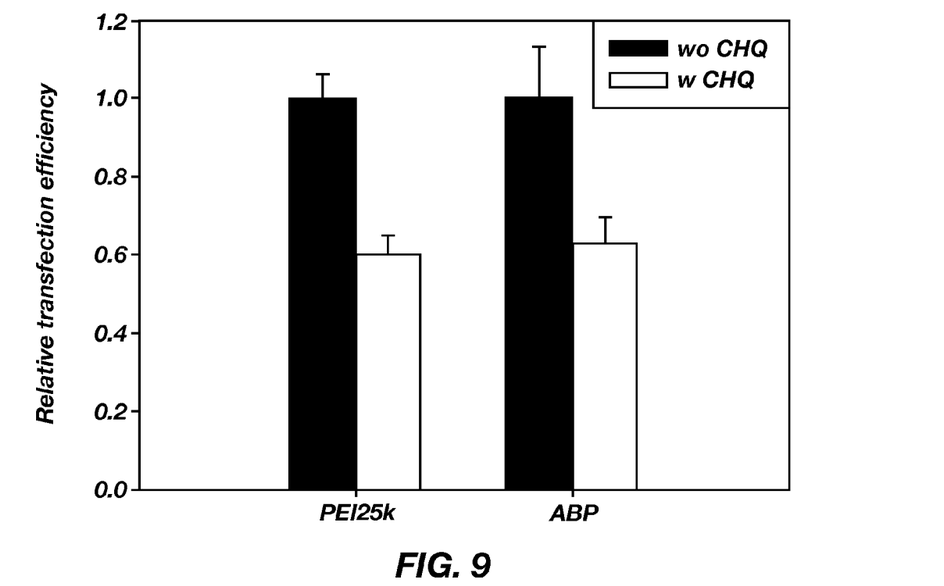
FIG. 9 shows relative transfection efficiency in C2C12 cells of pDNA/PEI25k ("PEI25k") and pDNA/ABP ("ABP") polyplexes in the absence (dark bars) and presence (open bars) of 100 μM chloroquine ("CHQ").

As shown in FIG. 9, transfection efficiencies of both PEI25k and ABP were found to be reduced to about 60% in the presence of chloroquine in comparison with the efficiencies in the absence of chloroquine. This result shows that 100

µM chloroquine does not improve the transfection of these polymers. PEI25k has various internal amines that can act as endosome buffers, and a slight decrease of transfection efficiency of PEI25k in treatment of chloroquine has been already reported. A. Akinc et al., Exploring polyethylenimine mediated DNA transfection and the proton sponge hypothesis, 7 J. Gene Med. 657-663 (2005). It was also suggested that the backbone polymer of ABP, poly (CBA-DAH), can have endosome buffering moieties. M. Ou et al., supra. Therefore, it is proposed that ABP can function as endosome buffer itself. However, this result does not explain the greatly enhanced transfection of ABP in comparison with poly(CBA-DAH).

Next, the cellular uptake of polyplexes was investigated by flow cytometry. YOYO-1 iodide-labeled pDNA was used for fluorescence measurements and poly(CBA-DAH) was used as a control polymer. After treatment of polyplexes, the cells were incubated in 0.4% trypan blue solution for 5 min to quench the fluorescence of extra-cellular polyplexes.

C2C12 cells were seeded at a density of $2 \times 10^5$ cells/well in a 6-well plate in DMEM medium containing 10% FBS and grown to reach 70-80% confluence prior to transfection. Before transfection, the medium in each well was exchanged for fresh serum-free medium. Plasmid DNA was labeled with YOYO-1 iodide (1 molecule of the dye per 100 base pairs of the nucleotide). M. Ogris et al., A versatile assay to study cellular uptake of gene transfer complexes by flow cytometry, 1474 Biochim. Biophys. Acta 237-143 (2000). The cells were treated with polyplex solutions (1 µg pDNA) at different weight ratios for 4 h at 37° C. Then, medium was aspirated from the wells, and the cells were washed two times with ice-cold DPBS. To quench the fluorescence of polyplexes adsorbed on the cell surface, the cells were incubated with 0.4% trypan blue solution for 5 min and washed with DPBS again. S. Sahlin et al., Differentiation between attached and ingested immune complexes by a fluorescence quenching cytofluorometric assay, 60 J. Immunol. Methods 115-124 (1983). After trypsinization, the cells were collected by centrifuge at 1500 rpm and suspended in 1 mL DPBS.

The cellular uptake of fluorescence-labeled polyplexes were examined using the BD FACScan analyzer (Becton Dickinson, San Jose, Calif.) at a minimum of $1 \times 10^4$ cells gated per sample. Analysis was performed by using Becton Dickinson CellQuest software.

Figure 10:
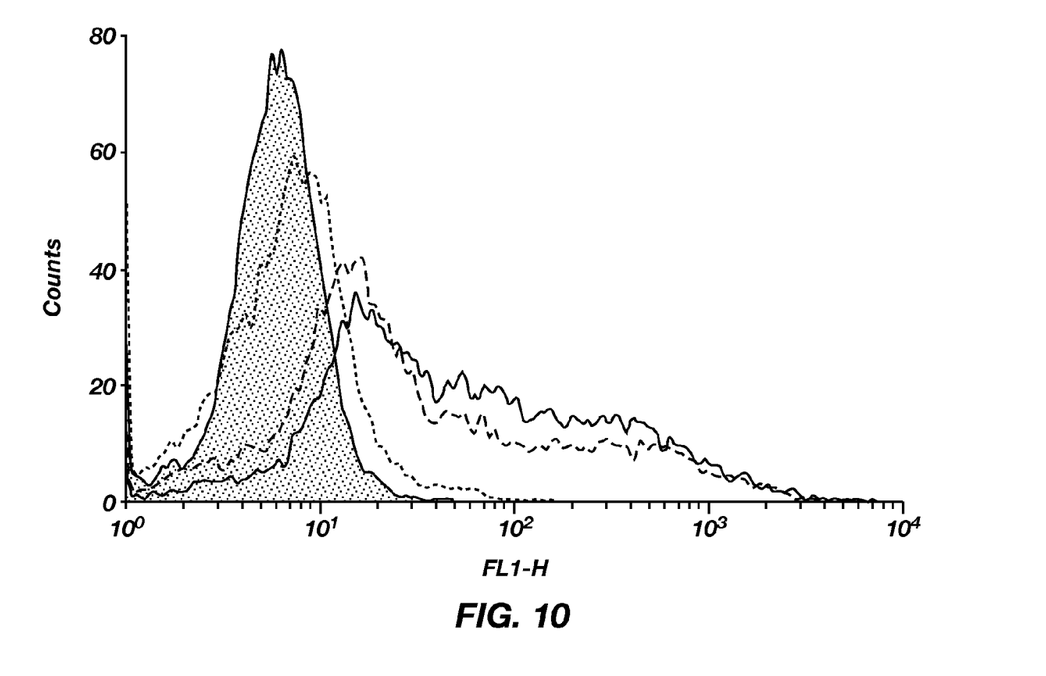
FIG. 10 shows cellular uptake results in C2C12 cells as measured by flow cytometry where the shaded peak shows cells only, the dotted line shows pDNA only, the dashed line shows pDNA/poly(CBA-DAH) polyplexes, and the solid bold line shows pDNA/ABP polyplexes.

As shown in FIG. 10, there seems to be no significant difference of fluorescence peaks between the poly(CBA-DAH) and ABP polyplexes despite their structural differences. This result means that conjugated arginine residues don't have any significant functions for cellular uptake of ABP polyplex. Therefore, it is interpreted that greatly enhanced transfection efficiency of ABP is not induced by its high cellular penetrating ability, but may be mediated by other factors such as good nuclear localization ability.

Example 7

In this example, the procedure of Example 1 is followed except that tert-butyl N-(2-aminoethyl)carbamate (N-Boc-1,2-diaminoethane, N-Boc-DAE) is substituted for tert-butyl-N-(6-aminohexyl)carbamate (N-Boc-1,6-diaminohexane, N-Boc-DAH).

Example 8

In this example, the procedure of Example 1 is followed except that tert-butyl N-(4-aminobutyl)carbamate (N-Boc-1,4-diaminobutane, N-Boc-DAB) is substituted for tert-butyl-N-(6-aminohexyl)carbamate (N-Boc-1,6-diaminohexane, N-Boc-DAH).

The subject matter claimed is:

1. A gene delivery carrier comprising an arginine-grafted bioreducible polymer, wherein the gene delivery carrier is represented by the formula wherein n is about 1 to about 1000; $R^1$ is $(CH_2)_m NH$, wherein m is about 1 to about 18; and $R^2$ is an arginine residue.

2. The composition of claim 1 wherein $R^1$ is $(CH_2)_6 NH$.
3. The composition of claim 1 wherein $R^1$ is $(CH_2)_4 NH$.
4. The composition of claim 1 wherein $R^1$ is $(CH_2)_2 NH$.
5. A complex comprising a selected nucleic acid bonded to an arginine-grafted bioreducible polymer, wherein the arginine-grafted bioreducible polymer is represented by the formula wherein n is about 1 to about 1000; $R^1$ is $(CH_2)_m NH$, wherein m is about 1 to about 18; and $R^2$ is an arginine residue.

6. The complex of claim 5 wherein $R^1$ is $(CH_2)_6 NH$.
7. The complex of claim 5 wherein $R^1$ is $(CH_2)_4 NH$.
8. The complex of claim 5 wherein $R^1$ is $(CH_2)_2 NH$.
9. The complex of claim 5 wherein the selected nucleic acid comprises a plasmid.
10. The complex of claim 5 wherein the selected nucleic acid comprises an oligonucleotide.

* * * * *